United States Patent [19]

Nakajima et al.

[11] Patent Number: 4,860,712
[45] Date of Patent: Aug. 29, 1989

[54] METHOD OF CONTROLLING AN OXYGEN CONCENTRATION SENSOR

[75] Inventors: Toyohei Nakajima; Toshiyuki Mieno, both of Wako, Japan

[73] Assignee: Honda Giken Kogyo Kabushiki Kaisha, Tokyo, Japan

[21] Appl. No.: 189,183

[22] Filed: May 2, 1988

[30] Foreign Application Priority Data

Jul. 1, 1987 [JP] Japan .................. 62-164394
Jul. 1, 1987 [JP] Japan .................. 62-164395

[51] Int. Cl.$^4$ ............. G01N 27/46; F02M 51/00; F02D 41/14
[52] U.S. Cl. .................. 123/489; 123/440; 204/1 T; 204/425; 204/400
[58] Field of Search .......... 123/489, 440; 73/23; 364/431.05; 204/1 T, 408, 412, 195 S, 425, 426, 406

[56] References Cited

U.S. PATENT DOCUMENTS

| | | | |
|---|---|---|---|
| 4,332,225 | 6/1982 | Cox et al. | 204/424 |
| 4,464,244 | 8/1984 | Uchida et al. | 204/426 |
| 4,500,412 | 2/1985 | Takahashi et al. | 204/425 |
| 4,611,562 | 9/1986 | Nakano et al. | 123/440 |
| 4,715,343 | 12/1987 | Kinoshita | 123/489 |
| 4,732,128 | 3/1988 | Yoshioka et al. | 123/489 |
| 4,741,312 | 5/1988 | Ohishi | 123/489 |
| 4,751,907 | 6/1988 | Yamamoto et al. | 123/489 |
| 4,753,204 | 6/1988 | Kojima et al. | 123/489 |
| 4,765,298 | 8/1988 | Kojima et al. | 123/489 |
| 4,773,376 | 9/1988 | Uchikawa et al. | 123/489 |

Primary Examiner—Raymond A. Nelli
Attorney, Agent, or Firm—Birch, Stewart, Kolasch & Birch

[57] ABSTRACT

A method for controlling an oxygen concentration sensor in which the supply of a heater current to a heater element is started when the complete combustion of the engine is detected. The supply of a pump current to an oxygen pump element is started when an internal resistance of the heater element is determined to be in a predetermined range. The supply of the pump current is started when the temperature of the oxygen pump element and the sensor cell element becomes sufficiently high to prevent the pump current from flowing excessively, thereby preventing the generation of blackening phenomenon.

3 Claims, 3 Drawing Sheets

METHOD OF CONTROLLING AN OXYGEN CONCENTRATION SENSOR

BACKGROUND OF THE INVENTION

1. Field of the Invention

The present invention relates to a method of controlling an oxygen concentration sensor mounted in the exhaust system of an internal combustion engine for sensing the oxygen concentration in the exhaust gas of the engine.

2. Description of Background Information

Conventional systems for controlling the air/fuel use a feedback operation, in which the oxygen concentration in the exhaust gas of an engine is detected by an oxygen concentration sensor. The air/fuel ratio of the mixture being supplied to the engine is controlled to meet a target value by the feedback operation in response to an output signal of the oxygen concentration sensor. The purpose of this control scheme is to purify the exhaust gas and improve the fuel economy.

A typical oxygen concentration sensor used in such air/fuel ratio control systems is capable of producing an output signal whose level is proportional to the oxygen concentration in the exhaust gas of the engine. For example, in Japanese Patent Application Laid Open No. 59-192955, an oxygen concentration sensor is disclosed which includes a pair of flat oxygen ion conductive solid electrolyte members each of which is provided with a pair of electrodes. These members form an oxygen pump element and a sensor cell element respectively, and are arranged in a manner such that a gas retaining chamber acting as a gas diffusion restriction region, is formed between the oxygen pump element and the sensor cell element. Thus, the formed gas retaining chamber communicates with the flow of a gas under measurement through a communication hole, while the surface of the other electrode of the sensor cell element communicates with an atmospheric air chamber.

In this type of oxygen concentration sensor, a pump voltage according to a voltage difference between a voltage generated across the electrodes of the sensor cell element and a reference voltage is applied to the oxygen pump element. This pump voltage causes oxygen ions in the oxygen pump element to move toward the electrode facing the restriction region when the voltage generated across the electrodes of the sensor cell element is higher than the reference voltage. On the other hand, when the voltage difference between the voltage generated across the electrodes of the sensor cell element is equal to or lower than the reference voltage, the pump voltage is applied to the oxygen pump element causiing the oxygen ions, in the oxygen pump element, to move toward an outer electrode. By this operation, the value of a current flowing across the electrodes of the oxygen pump element, that is the pump current becomes proportional to the oxygen concentration in the gas supplied to the diffusion restriction region for air/fuel ratios both in the lean and rich regions.

When using oxygen concentration sensors of such a kind, it was discovered that the supply of an excessive pump current causes a blackening phenomenon. This is realized when the amount of oxygen is the diffusion restriction region is smaller than an amount which can be pumped out by the pump current, thereby causing oxygen to be removed fromthe solid electrolyte. When Zr (zirconium dioxide) is used as the solid electrolyte, oxygen $O_2$ is removed from $ZrO_2$ by supplying excessive current to the oxygen pump element, so that zirconium Zr is separated out.

Moreover, when using the oxygen concentration sensors of the oxygen-concentration proportional type which has been described above, it is necessary that the temperature of the oxygen concentration sensing element is sufficiently higher than (for example, higher than 650° C.) the temperature of the exhaust gas under a steady operation of the engine to obtain an output signal characteristic which is proportional to the oxygen concentration. In other words, it is necessary to activate the solid electrolyte to cause a good conductivity of oxygen ions. Therefore, a heater element for heating the oxygen concentration sensing element is provided in an appropriate position with respect to the solid electrolyte. Thus, the feedback control of air/fuel ratio is executed by using the output signal of the oxygen concentration sensing element when the oxygen concentration sensing element is heated to a sufficiently high temperature. This type of air/fuel ratio control system is disclosed, for example, in U.S. Pat. No. 4,707,241.

Since generally the temperature of the oxygen concentration sensing element is low during the starting of the engine, it is desirable that the heating-up of the oxygen concentration sensing element is completed as quickly as possible. In addition, since the voltage generated across the electrodes of the sensor cell element is not raised sufficiently high under such a condition, there is a possibility that the pump current becomes excessive in the oxygen pump element such that the pump current is increased or decreased in accordance with a result obtained by comparing the voltage with the reference voltage.

Moreover, it is not possible to detect the temperature in the interior of the oxygen pump element and the sensor cell element. Therefore, conventionally it is estimated that an activated state, in which the oxygen pump element and the sensor cell element are heated by the heater element so that a desirable output characteristic of the proportional type is obtained, is reached when a predetermined time period has elapsed after the start of the supply of a heater current to the heater element. However, since the activated state is determined without respect to the actual temperature of the oxygen pump element and the sensor cell element, the activated state of the oxygen concentration sensor is not detected with enough accuracy.

OBJECTS AND SUMMARY OF THE INVENTION

A first objective of the present invention is therefore to provide a method for controlling an oxygen concentration sensor for an internal combustion engine by which the oxygen concentration sensing element is placed very quickly in an operable state immediately after starting of the engine, and which also avoids the blackening phenomenon.

A second objective of the present invention is to provide a method for controlling an oxygen concentration sensor for an internal combustion engine capable of detecting the activated state very accurately.

According to a first aspect of the present invention, a method for controlling an oxygen concentration sensor for an internal combustion engine is characterized by starting the supply of a heater current from a heater current supply means to a heater element when a predetermined starting state of the engine is detected, and subsequently starting the supply of a pump current from a pump current supply means to an oxygen pump element when it is detected that an internal resistance of the heater element has a value within a predetermined range.

According to a second aspect of the present invention, a method for controlling an oxygen concentration sensor for an internal combustion engine is characterized by starting the supply of a pump current from a pump current supply means to an oxygen pump element, and subsequently judging that the oxygen concentration sensor is in an activated state when a voltage across electrodes of a sensor cell element is in a first predetermined range and a voltage across electrodes of the oxygen pump element is in a second predetermined range.

DETAILED DESCRIPTION OF A PREFERRED EMBODIMENT

The embodiment of the present invention will be explained with reference to the accompanying drawings.

Figure 1:
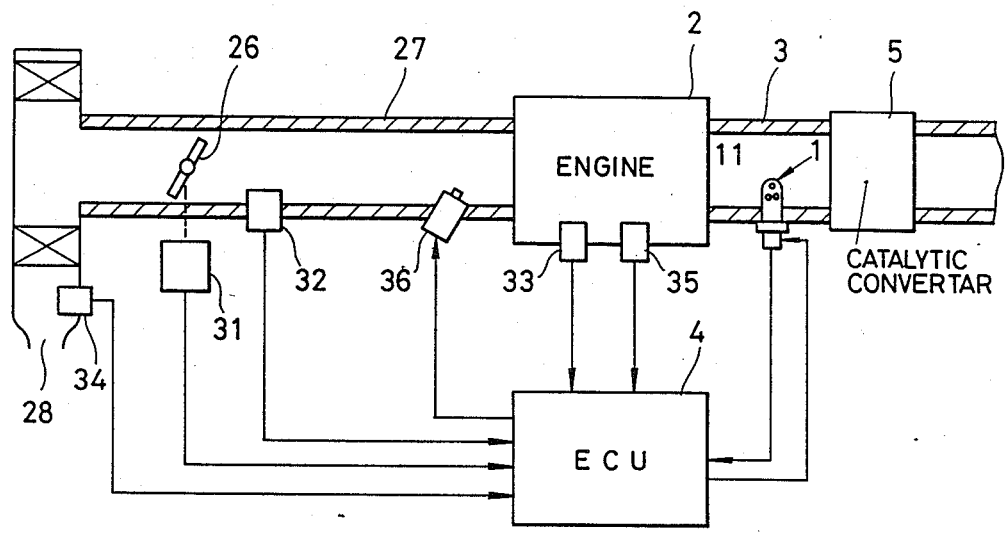
FIG. 1 is a schematic diagram showing an electronically controlled fuel injection system in which a method of controlling an oxygen concentration sensor is applied.
Figure 2:
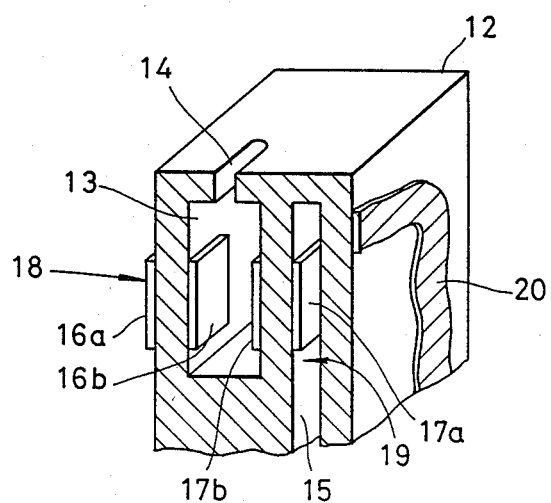
FIG. 2 is a view showing a detection part of the oxygen concentration sensor of the system shown in FIG. 1.
Figure 3:
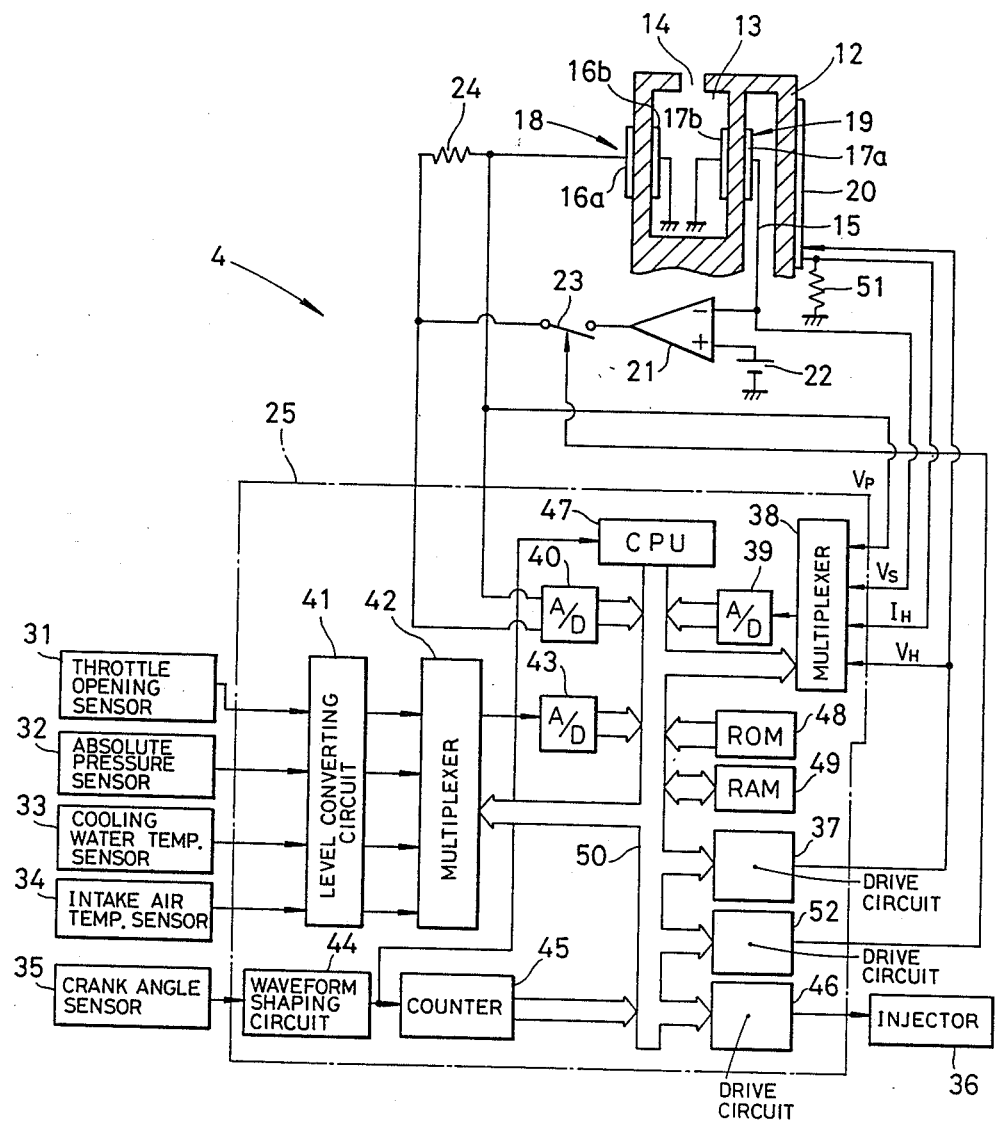
FIG. 3 is a block diagram showing the circuit in the ECU of the system shown in FIG. 1.

FIGS. 1 through 3 show an electronically controlled fuel injection system which is provided with an oxygen concentration sensor to which the control method according to the present invention is applied.

In this system, a detection part 1 of the oxygen concentration sensor is mounted in an exhaust pipe 3 of an engine 2, at a location which is upstream of a three-way catalytic converter 5. The input and output of the detection part 1 of the oxygen concentration sensor is connected to an EPU (Electronic Control Unit) 4.

In a protection case 11 of the detection part 1 of the oxygen concentration sensor, there is provided an oxygen ion conductive solid electrolyte member 12 having a general configuration of, for example, a rectangular parallelepiped as shown in FIG. 2. As shown in FIG. 2, the oxygen ion conductive solid electrolyte member 12 has a gas retaining chamber 13 which is formed as a gas diffusion restriction region. The gas retaining chamber 13 leads to a gas introduction hole 14 for introducing a gas under measurement, i.e., the exhaust gas of the engine, from the outside of the oxygen ion conductive solid electrolyte member 12. The gas introduction hole 14 is positioned in the exhaust pipe 3 so that the exhaust gas can easily flow into the gas retaining chamber 13. The oxygen ion conductive solid electrolyte member 12 is provided with a reference atmospheric air chamber 15 in to which atmospheric air is introduced. The reference atmospheric air chamber 15 is separated from the gas retaining chamber 13 by means of a wall between them. On the wall between the gas retaining chamber 13 and the reference atmospheric air chamber 15, and on the wall of the gas retaining chamber 13 opposite the atmospheric air chamber 15, there are provided respectively a pair of electrodes 17a and 17b and a pair of electrodes 16a and 16b. The solid electrolyte member 12 and the pair of electrodes 16a and 16b together operate as an oxygen pump element 18, and the solid electrolyte member 12 and the pair of electrodes 17a and 17b together operate as a sensor cell element 19. Furthermore, a heater element 20 is provided on an outside wall of the reference atmospheric air chamber 15 so that the oxygen pump element 18 and the sensor cell element 19 are heated.

In the oxygen ion conductive solid electrolyte 12, zirconium dioxide ($ZrO_2$) is used, and platinum (Pt) is used as the electrodes 16a through 17b.

As shown in FIG. 3, the ECU 4 includes a control unit for the oxygen concentration sensor which comprises a differential amplifier 21, a reference voltage source 22, and a current detecting resistor 24. The electrode 16b of the oxygen pump element 18 and the electrode 17b of the sensor cell element 19 are grounded. The differential amplifier 21 is connected to the electrode 17a of the sensor cell element 19 to produce an output voltage corresponding to the difference between a voltage generated across the electrodes 17a and 17b of the sensor cell element 19 and an output voltage of the reference voltage source 22. The output voltage of the reference voltage source 22 is a voltage (0.4 V for example) corresponding to the stoichiometric air/fuel ratio.

The output terminal of the differential amplifier 21 is connected to the electrode 16a of the oxygen pump element 18 through a switch 23, having a control terminal, and the current detecting resistor 24. Terminals of the current detecting resistor 24 operate as output terminals of the oxygen concentration sensor and are connected to a control circuit 25 which comprises a microcomputer. A heater current detecting resistor 51 is connected to the heater element 20, and a voltage is supplied across the series circuit of the heater element and the resistor 51 from a heater drive circuit 37. The heater drive circuit 37 includes a switching element (not shown) connected in series with the series circuit of the heater element 20 and the resistor 51.

A throttle opening sensor 31 is coupled to the control circuit 25 which for example, comprises a potentiometer and generates an output voltage whose level corresponds to the opening of a throttle valve 26. An absolute pressure sensor 32 provided in an intake pipe 27 on the downstream side of the throttle valve 26, which generates an output signal whose level corresponds to the absolute pressure in the intake pipe 27; a cooling water temperature sensor 33 which generates an output voltage whose level corresponds to the temperature of the cooling water of the engine 2; an intake air temperature sensor 34 provided near an atmospheric air inlet port 28 which generates an output having a level corresponding to the temperature of the intake air; and a crank angle sensor 35 which generates a pulse train signal synchronized with the rotation of the crankshaft (not shown) of the engine 2 are also coupled to the control circuit 25. Moreover, an injector 36 provided in the intake pipe 27 near the intake valves (not shown) of the engine 2 is also connected.

In addition to the above mentioned drive circuit 37, the control circuit 25 includes a multiplexer 38 which selectively outputs either the voltage across the terminals of the oxygen pump element 18, the voltage across the terminals of the sensor cell element 19, the voltage across the terminals of the heater element 20, or the voltage across the terminals of the current detection resistor 51; an A/D converter 39 which converts a signal outputted from the multiplexer 38 into a digital signal; an A/D converter 40 having a differential input, which converts the voltage across the terminal of the current detecting resistor 24 to a digital signal; a level converting circuit 41 which performs the level conversion of the output signals of the absolute pressure sensor 32 the cooling water temperature sensor 33; and the intake air temperature sensor 34, respectively; a multiplexer 42 which selectively outputs one of the output signals of the sensors through the level converting circuit 41; an A/D converter 43 which converts the signal signal outputted from the multiplexer 42 into a digital signal; a waveform shaping circuit 44 which performs the waveform shaping of the output signal of the crank angle sensor 35 and outputs it as a TDC signal; a counter 45 which detects the period of the TDC signal by counting the number of clock pulses applied from a clock pulse generating circuit (not shown); a drive circuit 52 which drives the switch 23; a drive circuit 46 which drives the injector 36; a CPU (central processing unit) 47 which executes digital operations according to programs; a ROM 48 in which various operation programs and data are previously stored; and a RAM 49.

The A/D converters 39, 40 and 43; the multiplexers 38 and 42; the counter 45; the drive circuits 37, 46 and 52, the CPU 47; the ROM 48; and the RAM 49 are mutually connected by means of an input/output bus 50. To the CPU signal is supplied from the waveform shaping circuit 44 to the CPU 47.

In addition, the RAM 49 is provided with a back-up power supply so that the stored content will not be extinguished when the ignition switch (not shown) is turned off.

With this construction, information corresponding to the voltage $V_P$ across the terminals of the oxygen pump element 18, the voltage $V_S$ across the terminals of the sensor cell element 19, the voltage $V_H$ across the terminals of the heater element 20; information corresponding to the heater current $I_H$ flowing through the heater element 20 from the A/D converter 39; the valve $I_P$ of the pump current flowing through the oxygen pump element 18 from the A/D converter 40; information corresponding to the opening $\theta$ th of the throttle valve, the absolute pressure $P_{BA}$ in the intake pipe, the cooling water temperature $T_W$, and the intake air temperature $T_A$ from the A/D converter 43 selectively; and information indicative of the count number within the period of generation of the rotation pulse from the counter 45 as the information of the engine rotational speed Ne are supplied to the CPU 47 through the input/output bus 50.

The CPU 47 reads the above mentioned various information in accordance with the program stored in the ROM 48, and calculates a fuel injection time $T_{OUT}$ of the injector 36 corresponding to the amount of fuel to be supplied to the engine 2 by using a predetermined calculating formula, in accordance with the information read and in synchronism with the TDC signal in a fuel supply routine. The injector 36 is actuated by the drive circuit 46 only during the fuel injection time $T_{OUT}$ so as to supply the fuel to the engine 2.

The fuel injection time $T_{OUT}$ is, for example, calculated by the following formula:

$$T_{OUT} = T_i \times K_{02} \quad (1)$$

where $T_i$ is a basic injection time, acting as a basic value of the air/fuel ratio control, determined by the data pump search of the ROM, according to the rotational speed Ne of the engine and the absolute pressure $P_{BA}$ in the intake pipe $K_{02}$ is a feedback correction coefficient of the air/fuel ratio which is set in response to the output signal level of the oxygen concentration sensor. These values $T_i$ and $K_{02}$ are set in subroutines (not shown) of the fuel supply routine, respectively. In addition, it is conceivable to use further correction coefficients such as an acceleration increment coefficient, an engine temperature coefficient. However, explanation of those coefficients is omitted for the purpose of simplicity.

Figure 4:
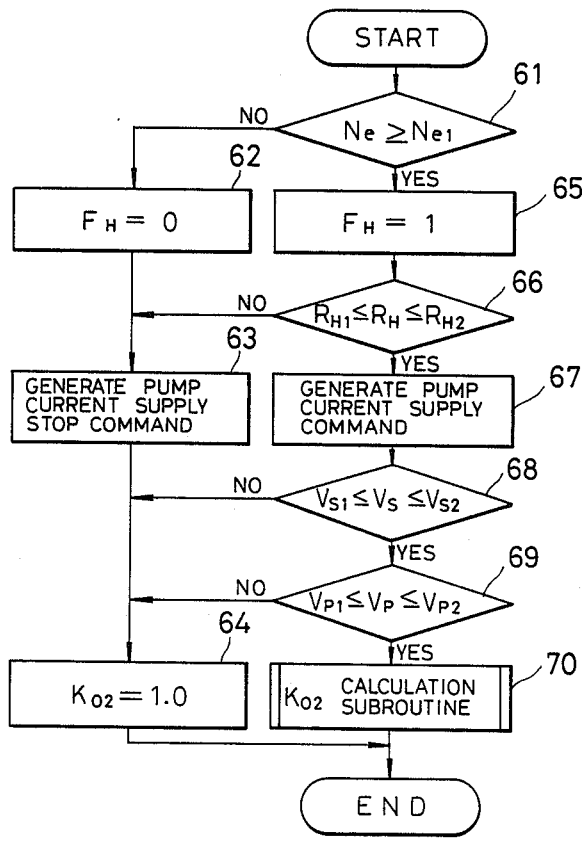
FIG. 4 is a flowchart showing the operation of the CPU.

The steps of the air/fuel ratio control method according to the present invention will be explained with reference to the flowchart showing the operation of the CPU which is illustrated in FIG. 4.

The CPU 47 at first reads the engine rotational speed Ne and determines as to whether or not the engine rotational speed Ne has exceeded a reference speed $Ne_1$ for complete combustion in the engine (400 rpm for example), at a step 61. If $Ne < Ne_1$, indicating that the oxygen concentration sensor is not in the activated state, the CPU 47 reset a heater current supply flag $F_H$ to 0 at step 62 so as to inhibit the supply of the heater current, and issues a pump current supply stop command to the switch drive circuit 52 at step 63. Then the CPU 47 makes the feedback correction coefficient $KO_2$ equal to 1.0 in order to stop the feedback control of the air/fuel ratio at step 64. Since the heater current supply flag $F_H$ is made equal to 0, heater current supply data indicating $I_H = 0$ is supplied to the heater drive circuit 37 by a heater current control subroutine (not shown) which is executed by the CPU 47 at predetermined intervals. Therefore, the heater drive circuit 37 turns-off the switching element incorporated therein, thereby stopping the supply of the heater current to the heater element 20. In response to the pump current supply stop command, the switch drive circuit 52 turns-off the switch 23, and accordingly the supply of the pump current to the oxygen pump element 18 is stopped.

When $Ne \geq Ne_1$, indicating that the complete combustion in the engine 2 is taking place, a value 1 is set to the heater current supply flag $F_H$ at step 65 so as to start the supply of the heater current. When the value 1 is set to the flag $F_H$, heater current supply data is determined at predetermined intervals so as to maintain the internal resistance $R_H$ of the heater element 20 constant, and supplied to the heater drive circuit 37, through the execution of the above mentioned heater current control subroutine. The switching element is turned on and off with a duty ratio corresponding to the content of the heater current supply data, at predetermined intervals.

When the switching element is turned on, the voltage $V_B$ is applied across the terminals of the series circuit of the heater element 20 and the current detecting resistor 51. The heater current flows through the heater element 20, so that heat is generated by the heater element 20. Then, the CPU 47 determines whether or not the internal resistance $R_H$ of the heater element 20 is in a range between predetermined values $R_{H1}$ and $R_{H2}$, at step 66. The voltage $V_H$ across the terminals of the heater element 20 and the value of the heater current $I_H$ are measured, and the internal resistance $R_H$ of the heater element 20 is calculated by using an equation of $R_H = (V_H - I_H)/I_H$.

If $R_H < R_{H1}$ or $R_H > R_{H2}$, indicating that the oxygen concentration sensor is not activated, and the program proceeds to steps 63 and 64. If $R_{H1} \leq R_H \leq R_{H2}$, indicating that the temperature of the heater element 20 has reached a stable temperature, the CPU 47 issues the pump current supply command to the switch drive circuit 52, at step 67, so that the pump current is supplied to the oxygen pump element 18. In response to the pump current supply command, the switch drive circuit 52 turns-on the switch 23, and the pump current is supplied to the oxygen pump element 18. After the supply of the pump current to the oxygen pump element 18 is started, the voltage $V_S$ across the electrodes of the sensor cell element 19 is measured. At step 68, it is determined whether or not the voltage $V_S$ is in a range between predetermined voltages $V_{S1}$ and $V_{S2}$ ($V_{S1} < V_{S2}$). Also, the voltage $V_P$ across the electrodes of the oxygen pump element 18 is measured. At step 69, it is determined whether or not the voltage $V_P$ is a voltage in a range between predetermined voltages $V_{P1}$ and $V_{P2}$ ($V_{P1} < V_{P2}$). If $V_S < V_{S1}$ or $V_S > V_{S2}$, indicating that the oxygen concentration sensor is not activated, the program proceeds to step 64. Also, if $V_P < V_{P1}$, or $V_P > V_{P2}$ even though $V_{S1} \leq V_S \leq V_{S2}$, indicating that the oxygen concentration sensor is not activated, the program proceeds to step 64. When $V_{S1} \leq V_S \leq V_{S2}$ and $V_{P1} \leq V_P \leq V_{P2}$ are satisfied at the same time, indicating that the temperature of the oxygen pump element 18 and the sensor cell element 19 has reached the predetermined voltage, and the elements are activated, the $K_{O2}$ subroutine is executed to calculate the air/fuel ratio feedback correction coefficient $K_{O2}$ at step 70, so that feedback control of air/fuel ratio is accomplished.

In the oxygen concentration sensor, after the supply of the pump current to the oxygen pump element 18 is started, the voltage $V_S$ generated across the electrodes 17a and 17b of the sensor cell element 19 becomes lower than the output voltage Vr of the reference voltage source 22 when the air/fuel ratio of the mixture supplied to the engine 2 is in the lean range. Under this condition, the output signal level of the differential amplifier 21 has a positive level. This positive level voltage is applied to the series circuit of the resistor 24 and the oxygen pump element 18. Since the pump current flows from the electrode 16a to the electrode 16b in the oxygen pump element 18, oxygen in the gas retaining chamber 13 is ionized at the electrode 16b, moved through the oxygen pump element 18, and released in the form of oxygen gas, at the electrode 16a. The oxygen in the gas retaining chamber 13 is pumped-out in this manner.

By pumping-out the oxygen in the gas retaining chamber 13, a difference in the oxygen concentration will be generated between the exhaust gas in the gas retaining chamber 13 and the atmospheric air in the reference atmospheric air chamber 15. The voltage $V_S$ corresponding to this difference in the oxygen concentration develops across the electrodes 17a and 17b of the sensor cell element 19 and is supplied to the inverting input terminal of the difference amplifier 21. Since the output voltage of the difference amplifier 21 is a voltage proportional to the difference voltage between the voltage $V_S$ and the output voltage Vr of the reference voltage source 22, the value $I_P$ of the pump current becomes proportional to the oxygen concentration in the exhaust gas. Thus the pump current value $I_P$ is determined with respect to the voltage present across the terminals of the current detecting resistor 24.

When the air/fuel ratio is in the rich region, the voltage $V_S$ exceeds the output voltage Vr of the reference voltage source 22. Therefore, the output signal level of the differential amplifier 21 turns from the positive level to a negative level. This negative level causes the pump current flowing through the electrodes 16a and 16b of the oxygen pump element 18 to decrease and the direction of the flow of the current to reverse. In other words, the pump current flows from the electrode 16b towards the electrode 16a, so that oxygen in the outside is ionized at the electrode 16a moved through the oxygen pump element 18, and released into the gas retaining chamber 13 in the form of oxygen gas at the electrode 16b. Therefore, the oxygen can be pumped in or out by supplying the pump current in such a manner as to maintain the oxygen concentration in the gas retaining chamber 13 constant. Thus, the pump current value $I_P$ becomes proportional to the oxygen concentration in the exhaust gas both in the lean and rich regions of the air/fuel ratio. In accordance with this pump current value $I_P$, the above mentioned feedback correction coefficient $K_{O2}$ is determined through the $K_{O2}$ calculation subroutine.

It will be appreciated from the foregoing, in the method for controlling an oxygen concentration sensor according to the first feature of the present invention, the supply of the heater current to the heater element is started when the complete combustion takes place in the engine, to rapidly heat up the oxygen concentration sensing unit which comprises a pump element and a sensor cell element by the generation of heat from the heater element. Subsequently the supply of the pump current to the oxygen pump element is started when the internal resistance of the heater element has risen to a level in a predetermined range corresponding to the temperature rise of the heater element. Thus, the supply of the pump current to the oxygen pump element is started when the temperature of the heater element, that is the temperature of the oxygen concentration sensing unit, has risen sufficiently, and an excessive flow of the pump current is prevented, so that generation of the blackening phenomenon is avoided.

According to the second feature of the present invention, in the method for controlling an oxygen concentration sensor, the temperature of each element is estimated to have reached a temperature at which a desirable proportional output characteristic can be obtained when the voltage across the electrodes of the sensor cell element is in the first predetermined range and the voltage across the electrodes of the oxygen pump element is in the second predetermined range, after the start of the supply of the pump current to the oxygen pump element, thereby the activated state of the oxygen concentration sensor is accurately determined.

What is claimed is:

1. A method for controlling an oxygen concentration sensor having an oxygen concentration sensing unit mounted in an exhaust system of an internal combustion engine, the oxygen concentration sensing unit including an oxygen pump element and a sensor cell element, each element being made of an oxygen ion conductive solid electrolyte and electrodes sandwiching the solid electrolyte, these elements forming a gas diffusion restriction region, a pump current supply device supplying a pump current to the electrodes of the oxygen pump element, a heater element for heating the oxygen concentration sensing unit by a heater current supplied thereto, and a heater current supply device supplying the heater current to the heater element, comprising the steps of:
- a first detection step for detecting a predetermined starting state of the engine;
- a first command step for starting the supply of the heater current from the heater current supply device to the heater element when the predetermined starting state is detected by said first detection step;
- a second detection step for detecting a condition when an internal resistance of the heater element is in a predetermined range after an execution of said first command step; and
- a second command step for starting the supply of the pump current from the pump current supply device to the oxygen pump element when said condition is detected by said second detection step.

2. The method as claimed in claim 1, wherein said first detection step is a step for detecting that a rotational speed of the engine has exceeded a rotational speed under a complete combustion state of the engine.

3. A method of controlling an oxygen concentration sensor having an oxygen concentration sensing unit mounted in an exhaust system of an internal combustion engine, the oxygen concentration sensing unit including an oxygen pump element and a sensor cell element, each element being made of an oxygen ion conductive solid electrolyte and electrodes sandwiching the solid electrolyte, these elements forming a gas diffusion restriction region, a pump current supply device supplying a pump current to the electrodes of the oxygen pump element so that a voltage generated across the electrodes of the sensor cell element becomes equal to a reference voltage, a heater element for heating the oxygen concentration sensing unit by a heater current supplied thereto, and a heater current supply device supplying the heater current to the heater element, comprising the steps of:
- a command step for starting the supply of the pump current from the pump current supply device to the oxygen pump element;
- a detection step for detecting a condition when the voltage across the electrodes of the sensor cell element is in a first predetermined range and a voltage across the electrodes of the oxygen pump element is in a second predetermined range after an execution of said command step; and
- a judging step for judging that the oxygen concentration sensor is in an activated state when said condition is detected by said detection step.

* * * * *